US011880436B2

(12) United States Patent
Fine et al.

(10) Patent No.: US 11,880,436 B2
(45) Date of Patent: Jan. 23, 2024

(54) REMOTE ACCESS CONTROL FOR DIGITAL HARDWARE

(71) Applicants: Eran Fine, Tel Aviv (IL); Nitzan Daube, Tel Aviv (IL)

(72) Inventors: Eran Fine, Tel Aviv (IL); Nitzan Daube, Tel Aviv (IL)

(73) Assignee: Nanolock Security Inc., Nitzanei Oz (IL)

(*) Notice: Subject to any disclaimer, the term of this patent is extended or adjusted under 35 U.S.C. 154(b) by 933 days.

(21) Appl. No.: 16/265,215

(22) Filed: Feb. 1, 2019

(65) Prior Publication Data

US 2019/0294765 A1 Sep. 26, 2019

Related U.S. Application Data

(60) Provisional application No. 62/731,221, filed on Sep. 14, 2018, provisional application No. 62/713,701, filed on Aug. 2, 2018, provisional application No. 62/647,179, filed on Mar. 23, 2018.

(51) Int. Cl.
| | | |
|---|---|---|
| *G06F 21/00* | (2013.01) | |
| *G06F 21/30* | (2013.01) | |
| *H04L 9/40* | (2022.01) | |
| *G06F 21/32* | (2013.01) | |
| *G06F 21/33* | (2013.01) | |
| *H04L 67/56* | (2022.01) | |

(52) U.S. Cl.
CPC ............ *G06F 21/305* (2013.01); *G06F 21/32* (2013.01); *G06F 21/33* (2013.01); *H04L 63/0884* (2013.01); *H04L 67/56* (2022.05)

(58) Field of Classification Search
CPC ........ G06F 21/31; G06F 21/305; G06F 21/32; G06F 21/33; H04L 9/0894; H04L 63/0884; H04L 67/34; H04L 67/28
See application file for complete search history.

(56) References Cited

U.S. PATENT DOCUMENTS

| | | | |
|---|---|---|---|
| 9,092,628 B2 | 7/2015 | Barkan | |
| 10,484,174 B1* | 11/2019 | Bernat | H04L 9/321 |
| 2007/0067620 A1* | 3/2007 | Jevans | H04L 9/321 |
| | | | 713/156 |
| 2007/0118767 A1* | 5/2007 | Wolford | G06F 21/31 |
| | | | 713/193 |
| 2011/0154023 A1* | 6/2011 | Smith | G06F 21/74 |
| | | | 713/155 |
| 2011/0307724 A1* | 12/2011 | Shaw | G06F 21/78 |
| | | | 713/323 |
| 2013/0125249 A1 | 5/2013 | Sadovsky et al. | |
| 2013/0347084 A1* | 12/2013 | Malinowski | H04W 12/086 |
| | | | 726/6 |

OTHER PUBLICATIONS

European Search Report for European Patent Application No. 19771477.7 dated Oct. 15, 2021 (10 pages).

\* cited by examiner

*Primary Examiner* — Ghazal B Shehni
(74) *Attorney, Agent, or Firm* — Morgan, Lewis & Bockius LLP

(57) ABSTRACT

Security systems for microelectronic devices physically lock the hardware itself and serve as a first line of defense by preventing overwriting, modification, manipulation or erasure of data stored in a device's memory. Implementations of the security systems can respond to lock/unlock commands that do not require signal or software interactivity with the functionality of the protected device, and which therefore may be consistent across devices.

21 Claims, 6 Drawing Sheets

REMOTE ACCESS CONTROL FOR DIGITAL HARDWARE

CROSS-REFERENCE TO RELATED APPLICATIONS

This application claims priority to and the benefit of, and incorporates herein by reference in their entireties, U.S. Provisional Patent Application Nos. 62/647,179, filed on Mar. 23, 2018; 62/713,701, filed on Aug. 2, 2018; and 62/731,221, filed on Sep. 14, 2018.

FIELD OF THE INVENTION

In various embodiments, the present invention relates generally to security measures for electronic devices, and in particular to controlling access to hardware devices such as integrated circuits (ICs).

BACKGROUND

Processor-driven controllers have, like computers, become ubiquitous due to their convenience, processing capacity and/or data-storage capacity. "Embedded" controllers operate devices ranging from refrigerators to pacemakers, and today's automobiles are as much computational as mechanical systems. The very features that make such controllers attractive render them, and therefore the systems they control, vulnerable to attack. For example, for a "smart appliance" to offer its owner the convenience of remote monitoring and control, it must receive and respond to user commands. If a hacker can "spoof" the controller and obtain access, he may be able not only to misuse the appliance but potentially also obtain the user's private information.

Most existing systems for securing control devices from attack, such as encryption protocols and/or passwords, tend to be solely software-based. Such approaches can be highly specific to the protected system, which may itself evolve over time, and are vulnerable to hacking. They also generate latency and require CPU power. As a result, hardware-based solutions have become increasingly attractive across a range of platforms.

One approach physically locks the hardware itself and serves as a first line of defense by preventing overwriting, modification, manipulation or erasure of data stored in a device's memory. For example, the security device may passively "listen" on data lines of the protected device and, when a lock or unlock command is received (typically in conjunction with a valid authentication code), the security device physically blocks or allows passage of signals to and from the protected device. A representative system is illustrated in FIG. 1A. The host 100 includes a CPU 110 and a non-volatile memory (NVM) circuit 120, which the CPU 110 accesses via a read/write security module 130 that controls access to the 120. All of these components generally reside on the host device 100 itself. For example, the security module 130 may be implemented along with the NVM 120 on a discrete chip, or all three illustrated components 110-130 may reside on a single "system-on-chip" device. As shown in FIG. 1B, the security module can be analogized to a gate 140 with a gatekeeper 145, who permits access only upon receipt of a proper security credential 150.

While advantageous for many applications, this approach implies that gaining control of the host 100 can result in control of the protected memory 120 as well. This vulnerability may be exploited by persistent attacks that modify the behavior of the targeted host 120 permanently. For example, in "man in the middle" attacks, the attacker secretly relays and may alter the communication between two parties who believe they are directly communicating with each other—e.g., a payer and the payer's funding source. This allows the attacker to divert the transaction for his own benefit or acquire enough information about the payer to spoof the funding source and transfer funds from the payer's account. The vulnerability arises not due to any intrinsic deficiency in the design of the host 100, but as a result of permitting control signals to originate externally and reach the host 100 via common communication facilities.

SUMMARY

Embodiments of the present invention utilize an external or remote (e.g., server-based) resources to perform certain functions required for operation of the protected device. In particular, server-based resources can provide security-related services as broad as user authentication or as narrow as performing a specific function, e.g., verifying a biometric indicium. The remote resource can also combine authentication with additional tasks such as verifying and installing updates to control programming. Thus, embodiments of the invention deploy the gatekeeper function within the controlled hardware (e.g., NVM) while the authentication function is performed by an external entity, e.g., a server in communication with the host. Although the ensuing discussion focuses on NVM, this is for ease of presentation only; the invention may be utilized to protect any resource access by or via the CPU.

Preferably, the gatekeeper functionality physically locks the hardware itself and is compatible with virtually any digital device. It can serve as a first line of defense by preventing overwriting, modification, manipulation or erasure of data stored in the device's memory. Implementations of the invention can respond to lock/unlock commands that do not require additional signal or software interactivity with the functionality of the protected device, and which therefore may be consistent across devices. Advantageously, embodiments of the invention provide backward compatibility with bus architectures and other hardware typically utilized to interface with the protected device. Moreover, various implementations maintain high-speed access for the device being protected and result in virtually no signal latency, at least when the device is "unlocked."

Accordingly, in a first aspect, the invention pertains to a security system for servicing memory access requests from a client device including a network interface. In various embodiments, the security system comprises a protected device comprising memory and a lock unit connected thereto, the lock unit comprising a network interface, and an authentication server, wherein the lock unit is configured to (i) detect a memory access request from the client device, (ii) receive authentication data from the client and communicate the received authentication data to the authentication server via the network interface, and (iii) only upon receipt via the network interface of an authentication confirmation signal from the authentication server, cause the lock unit to allow the memory access request to be serviced.

The authentication data may be a password or certificate encrypted symmetrically or asymmetrically. Alternatively, the authentication data may be a biometric indicium. In various embodiments, the authentication signal specifies read access, read/write access or no access, and the processor is configured to responsively operate the lock unit in accordance with the authentication signal. The authentication server may in some embodiments, be remote from the protected device.

In another aspect, the invention relates to a protected digital device comprising, in various embodiments, a processor, a memory, a communication platform, a security system for servicing access requests to the memory, a lock unit connected to the memory, and a proxy system for establishing a trusted communication channel via the communication platform between the lock unit and an authentication server external to the protected digital device. The lock unit may be configured to (i) detect a memory access request from the processor, (ii) communicate authentication data to the authentication server via the trusted communication channel, and (iii) only upon receipt via the trusted communication channel of an authentication confirmation signal from the authentication server, cause the lock unit to allow the memory access request to be serviced.

The authentication data may be a password or certificate encrypted symmetrically or asymmetrically. Alternatively, the authentication data may be a biometric indicium. In various embodiments, the authentication signal specifies read access, read/write access or no access, and the processor is configured to responsively operate the lock unit in accordance with the authentication signal.

In some embodiments, the proxy system provides end-to-end encryption between the authentication server and the lock unit; for example, the proxy system may provide symmetric encryption between the authentication server and the lock unit. The proxy system may be configured to examine communications received from the authentication server for a digital signature.

Yet another aspect of the invention pertains to a security system for servicing memory access requests from a client device. In various embodiments, the security system comprises (a) on the client device, (i) a protected device comprising memory and a lock unit connected thereto, (ii) a proxy system, and (iii) a communication platform; and (b) a management server for performing a management function comprising receiving and processing signals from the client device, the communication platform including a proxy system for establishing a trusted communication channel between the management server and the lock unit. The lock unit may be configured to (i) detect a valid memory access request provided via the trusted communication channel, and (ii) allow the memory access request to be serviced and data transmitted to the management server over the trusted communication channel.

The trusted communication channel may be established, for example, via symmetric encryption or end-to-end encryption. The management server may be configured to provide an authentication function that includes receiving authentication data from the client device and allowing establishment of the trusted communication channel only following validation of the received authentication data. The memory access request includes data specifying read access, read/write access or no access, the lock unit responsively operating in accordance with the data included in the memory access request. In some embodiments, the lock unit is responsive only to write commands issued by the management server.

The client device may comprise a processor, with the lock unit being responsive only to write commands issued by the client processor only following receipt via the trusted channel of a valid memory access request including a write permission for the processor. The client device may be configured to generate telemetry data, cache the telemetry data in the protected device memory, and transmit the telemetry data to the management server via the trusted communication channel. In some embodiments, the client device comprises a processor that does not have access to the telemetry data.

In still another aspect, the invention relates to a controller comprising, in various embodiments, an output interface for causing performance of at least one control function; a protected memory including stored control instructions; a processor for executing the stored control instructions and operating the output interface in accordance therewith; a communication platform; a security device governing access to the protected memory; and a proxy system for establishing a trusted communication channel via the communication platform between the security device and an external management device. The security device may be configured to (i) detect a memory access request from the external device, (ii) authenticate a user of the external management device, and (iii) only upon receipt via the trusted communication channel of an authentication confirmation signal from the authentication server, cause the security device to allow the memory access request to be serviced.

In various embodiments, the controller further comprises an I/O interface for receiving sensor data for storage in the protected memory. The authentication data may be a password or certificate encrypted symmetrically or asymmetrically. Alternatively, the authentication data may be a biometric indicium. In various embodiments, the authentication signal specifies read access, read/write access or no access, and the processor is configured to responsively operate the lock unit in accordance with the authentication signal.

The proxy system may provide end-to-end or symmetric encryption between the authentication server and the lock unit. The proxy system may be configured to examine communications received from the authentication server for a digital signature.

In yet another aspect, the invention relates to an IoT device comprising, in various embodiments, a control module for performing a data-gathering or control function, a protected memory, a communication platform, a security device governing access to the protected memory, and a proxy system for establishing a trusted communication channel via the communication platform between the security device and an external management device. The security device may be configured to (i) detect a memory access request from the external device, (ii) authenticate a user of the external management device, and (iii) only upon receipt via the trusted communication channel of an authentication confirmation signal from the authentication server, cause the security device to allow the memory access request to be serviced.

The control module may be configured to perform a control function corresponding to control of a household system or a data-gathering function corresponding to image acquisition of a monitored area. The authentication data may be a password or certificate encrypted symmetrically or asymmetrically. Alternatively, the authentication data may be a biometric indicium. In various embodiments, the authentication signal specifies read access, read/write access or no access, and the processor is configured to responsively operate the lock unit in accordance with the authentication signal.

The proxy system may provide end-to-end or symmetric encryption between the authentication server and the lock unit. The proxy system may be configured to examine communications received from the authentication server for a digital signature.

As used herein, the terms "approximately," "roughly," and "substantially" mean ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

A. Remote Server Architectures

Figure 1A:
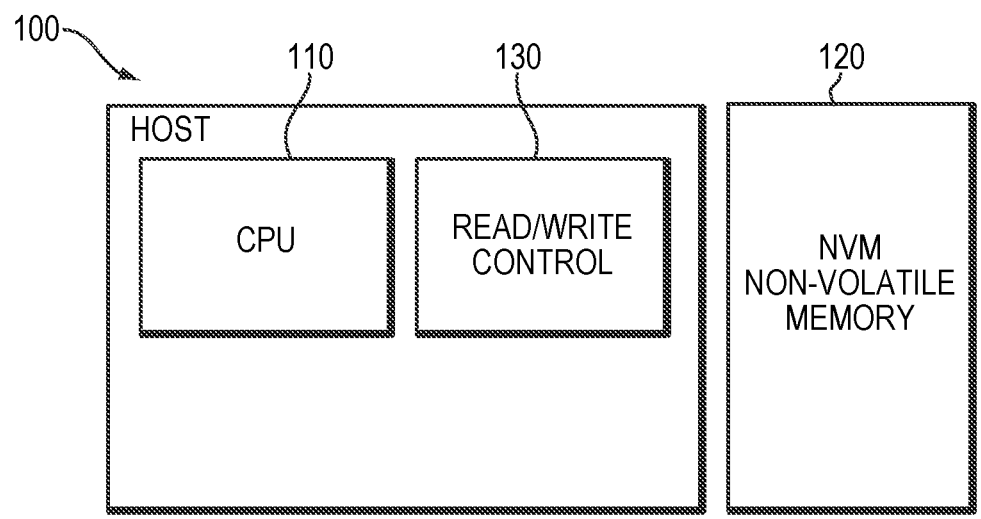
FIGS. 1A and 1B schematically illustrate prior-art security systems whose functionality is deployed entirely within a host device.
Figure 1B:
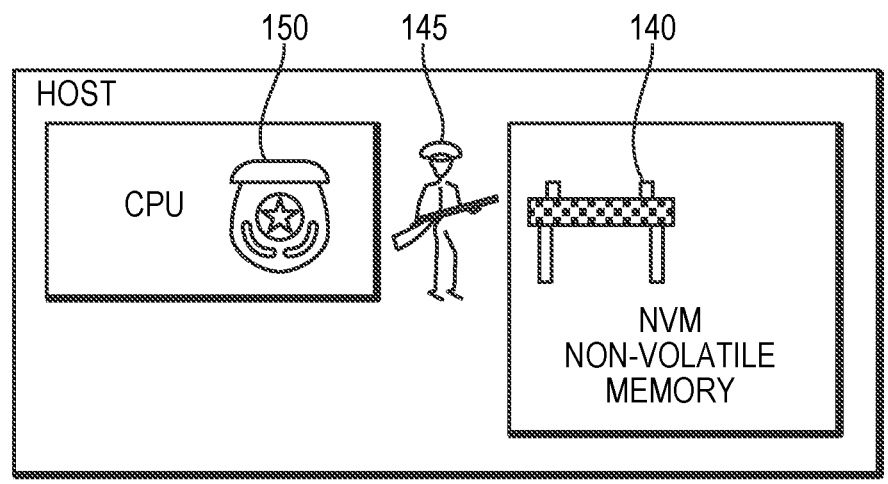
Figure 2A:
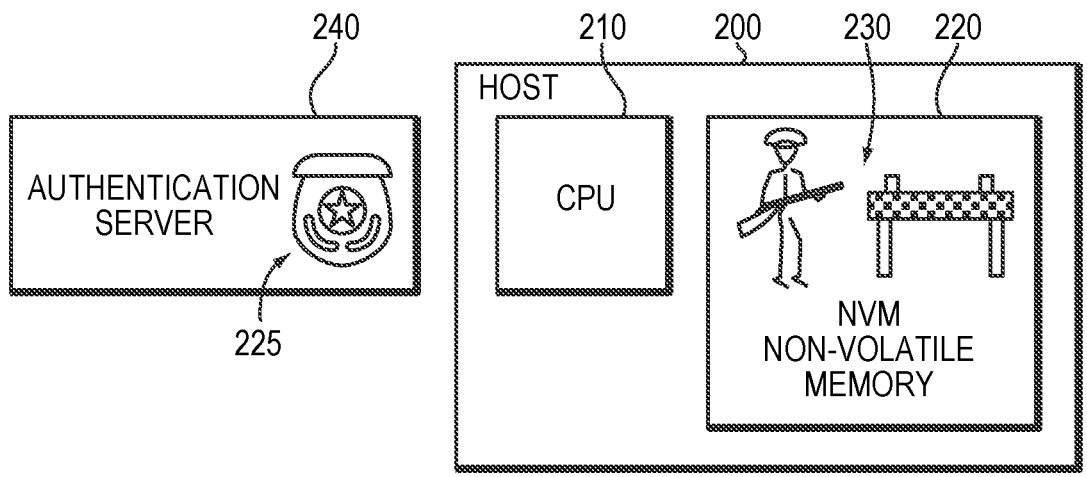
FIGS. 2A-2C schematically illustrate security systems that utilize an external authentication server.
Figure 2B:
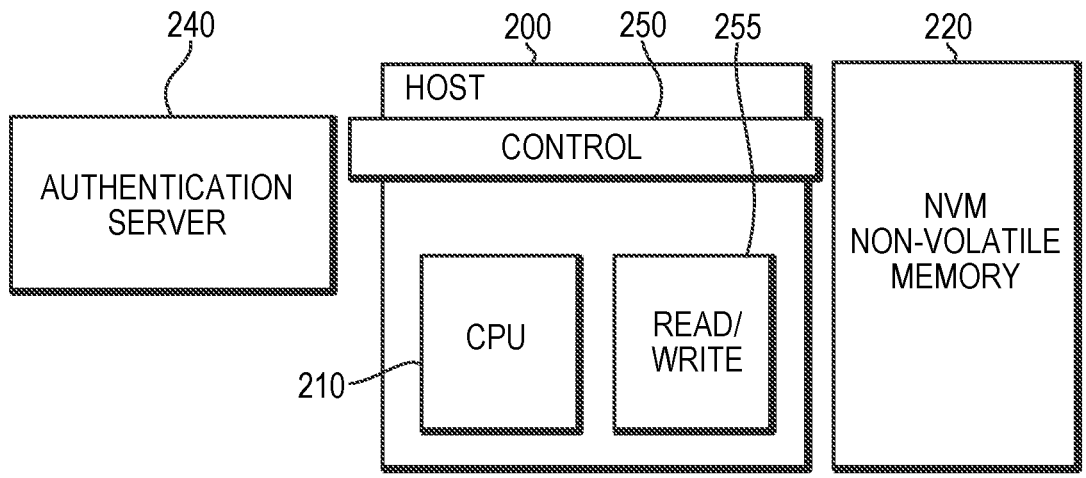

Refer first to FIG. 2A, which conceptually illustrates a host device 200 protected in accordance with embodiments of the invention. The host 200 includes conventional computational circuitry including a CPU 210, nonvolatile memory, peripherals, etc., and an NVM 220 protected by a gate and gatekeeper collectively indicated at 230. The certificate or key 235 necessary to satisfy the gatekeeper 230 does not reside on the host 200, as in the prior art, but instead is maintained by a remote authentication server 240. In effect, the host 200 serves as an intermediary between the protected functionality 220 and the authentication server 240. As shown in greater detail in FIG. 2B, a dedicated communication path 250 for control signals provides a secure conduit for control signals passed between the authentication server 240 and the read/write security module 255, which actually performs the function of the gate and gatekeeper 230. The authentication server 240 may communicate with the host 200 via wired or wireless connections, and via a computer network or the public telecommunications infrastructure. The authentication server 240 can provide end-to-end authentication or may perform a specific authentication function, e.g., verifying a biometric indicium such as a fingerprint scanned by the host 200. The communication path 250 is implemented in a manner that isolates it, logically or physically, from the CPU 210 so that hijacking the CPU is insufficient to gain access to the NVM 220 via the communication path 250 and the security module 255.

Figure 2C:
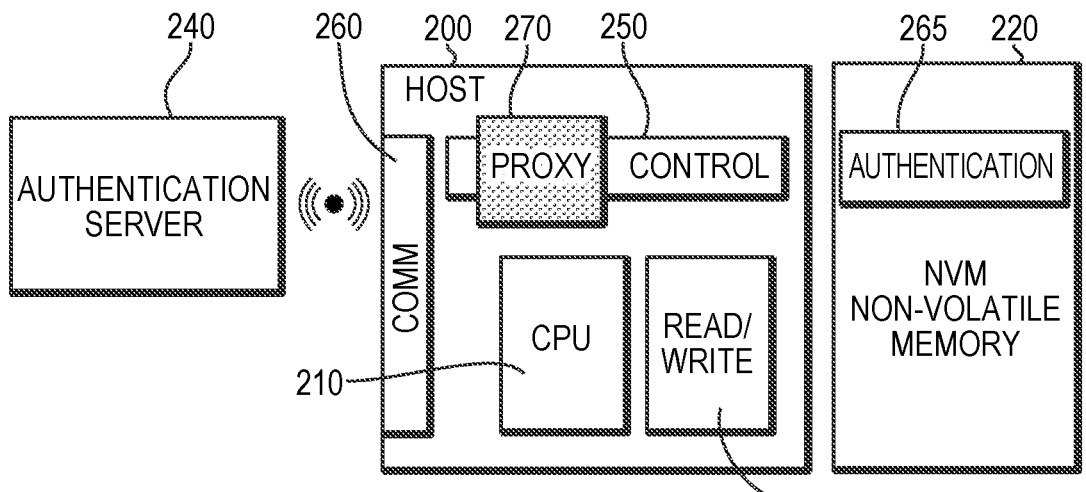

This is shown in FIG. 2C, which illustrates a wireless implementation. The authentication server communicates with the host 200 via a communications interface 260. Commands pass directly from the authentication server 240 to an authentication module 265 associated logically and/or physically with the NVM 220, bypassing the host operating system (and thereby the ability of intruders to manipulate commands or generate them via the host). The illustrated "proxy" functionality 270 behaves as a logical communication driver for the NVM authentication module 265. The host 200 includes a conventional communication platform implementing, for example, TCP/IP packet-based communication. The data contained in incoming message packets (arriving via the communication interface 260 and intended for the NVM authentication module 265) is handled by the proxy 270, which extracts the data and delivers it to the module 265. Similarly, any data produced by the module 265 for transmission to the authentication server 240 is handled initially by the proxy 270, which supplies it to the communication platform for encapsulation and transmission over TCP/IP. In one embodiment, all communication between the authentication server 240 and the NVM authentication module 265 is signed and the signature is enforced at the receiving end, by the module 265, to block attempts to modify the data transmitted between the NVM 220 and the authentication server 240. Alternatively, the authentication server 240 and the module 265 may implement end-to-end encryption. Either way, obtaining access to the message flow (by, e.g., hijacking the CPU 210) is insufficient to access the NVM 220 via the security module 255 due to the digital signature and/or encryption.

In operation, the NVM authentication module 265 detects memory access requests from the CPU 210. If authentication has not yet taken place during the current session, the NVM authentication module 265 prompts the CPU 210 to obtain authentication data via, for example, a fingerprint reader. Alternatively, this function of obtaining biometric data from the user may be performed by the NVM authentication module 265 itself. Once the authentication data has been provided, it is sent via the proxy 270 to the authentication server 240 over the network interface 260. Upon receipt via the network interface of an authentication confirmation signal from the authentication server 240, the authentication module 265 signals the security module 255 to allow the memory access request to be serviced. The security module 255 may accord the CPU 210 continued access to the NVM 220 in accordance with a security policy—e.g., access may persist throughout the current session, or may terminate following a fixed period of inactivity or in response to a walk-away or other detected event.

Figure 3A:
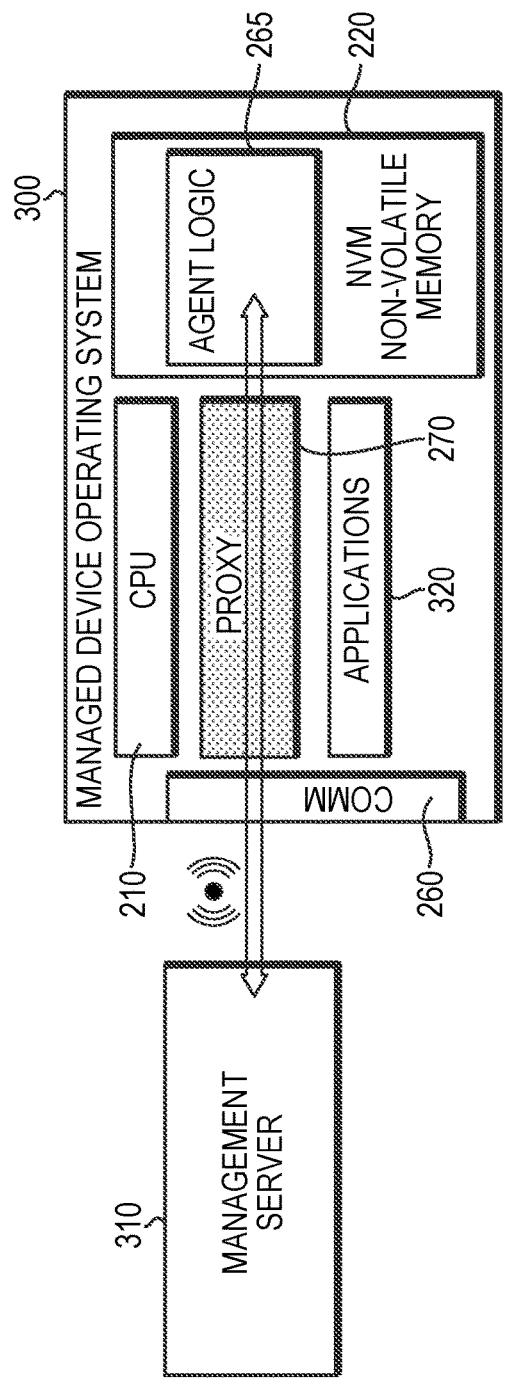
FIGS. 3A and 3B schematically illustrate security systems that utilize an external server performing both authentication and device-specific management functions.
Figure 3B:
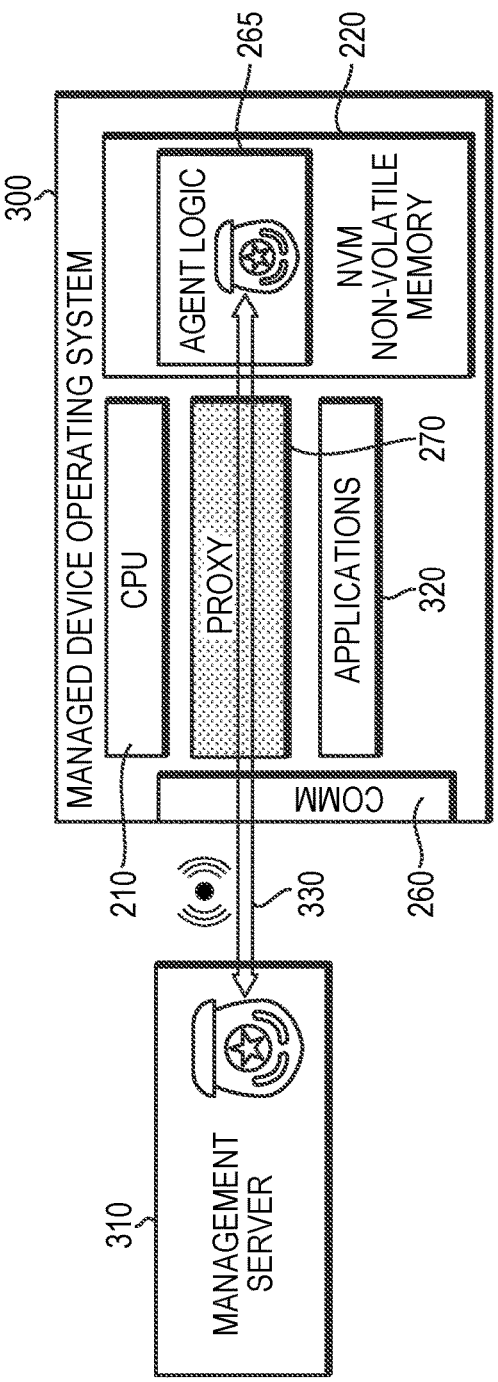

Outside servers may have roles other than, or in addition to, authentication. For example, the NVM may be in a managed device such as a surveillance camera, industrial controller, smart thermostat, alarm system or other monitored device or system. As shown in FIGS. 3A and 3B, a managed device 300 may communicate with a management server 310, which provides authentication for access to the NVM 220 as well as services specific to the functionality of the device 300. The read/write functionality of the NVM 220 is governed by an "agent" 265, which performs the functions of the authentication module 265 and the read/write security module 255 illustrated in FIG. 2C. Signals generated by the management server 310 and received and processed by device-specific applications 320 executed as running processes by the CPU 210, but signals directed specifically to the agent 265 reach it securely via the proxy 270 as described above. In some implementations, the contents of the NVM 220 may be written only by the management server 310 and not to the managed device's own CPU 210 (although the CPU 210 may read the contents of the NVM 220 in order to execute the program stored therein); in such implementations, hijacking the device will not enable an intruder to modify the contents of the NVM. In other implementations, the contents of the NVM 220 may be written by the CPU 210 following receipt via the proxy 270 of a valid memory access request including a write permission for the CPU 210. The write permission may be limited in time or scope, e.g., confined to a partition of the NVM 220.

A managed device 300 may send various types of data, or "telemetry," to the management server 310 periodically and/or in response to queries. The management server 310 may, for example, monitor device integrity and functionality by sending or receiving periodic "ping" messages to the monitored device 300, checking the status of device batteries by sending periodic queries or receiving periodic "Battery OK" transmissions from the device, or checking the device status (on, off, standby, etc.). Other telemetry data may include the NVM operation log (read, write, etc.); the gatekeeper operation log; the image version written to the protected NVM; and the NVM state, for example.

In some implementations, the management server 310 may also handle communications relevant to the dedicated application-level functionality of the monitored device 300, e.g., receiving video or still images, registering and reacting to intrusion detection signals from an alarm system, and/or reacting to conditions (e.g., temperature, pressure, flow rate or other condition monitored by an industrial controller) sensed by the device, e.g., by sending an alert to responsible personnel when a safety level is exceeded. To the extent they do not involve protected memory, however, these application-level messages are not secured by the agent 265.

To the extent that telemetry data resides or is cached in the NVM 220, it is provided directly to the management server 310 (e.g., periodically or upon request) via the proxy 270; as a result, even if the operating system of the managed device 300 has been hijacked or the device otherwise compromised, the telemetry data can neither be spoofed nor modified. If authentication is part of the communication protocol between the management server 310 and the monitored device 300, the management server 310 may handle the authentication function directly, in the manner described above, or may utilize an outside resource. In other deployments, authentication is handled by a separate server, communicating with the management server 310 or directly or with a separate authentication server (which may itself communicate directly with the monitored device or indirectly, via the management server). Following successful authentication (where necessary), the proxy 270 may take the form a trusted channel 330 between the management server 310 and the NVM agent 265 as illustrated in FIG. 3B. This trusted channel 330 may be based on a symmetric key shared by the management server 310 and the agent 265; public-key encryption, in which (for example) the management server retains the private key and provides the public key to all managed devices; or any combination thereof or suitable cryptographic alternative thereto. Thereafter, NVM memory contents (e.g., cached telemetry data) are provided via the proxy 270 using the trusted channel 330.

Thus, tampering with NVM data may prevented at the managed device 300 if the data passes directly from the proxy 270 to the communication platform 260 and thereafter to the communication channel 336 without opportunity for involvement of the managed device's CPU 210; and because the communication channel 330 is trusted and the data encrypted, tampering with the data following its exit and before it reaches the management server 310 is also precluded. It should be understood that the CPU 210 may be physically excluded from access to the NVM data if the NVM circuit 220 has its own processing hardware operating autonomously from the CPU 210 and implementing the proxy system 270. Alternatively, the proxy 270 may be implemented in code executed by the CPU 210 but all other programs executed by the CPU 210 may be logically excluded from access to data stored in the NVM 220.

The above configurations, in which the gatekeeper or agent communicates with external resources utilizing a network, is herein referred to as a "cloud" configuration. The external network may be a wired or wireless local-area network (LAN), wide-area network (WAN) and/or other types of networks. When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Computers may be connected over the Internet, an Intranet, Extranet, Ethernet, or any other system that provides communications. Some suitable communications protocols may include TCP/IP, UDP, or OSI, for example. For wireless communications, communications protocols may include Bluetooth, ZigBee, IrDa or other suitable protocol. Furthermore, components of the system may communicate through a combination of wired or wireless paths. For example, a large organization may manage its security infrastructure internally, in which case the authentication server 240, while remote and logically separate from the device 200 or 300 may nonetheless be located mere feet away and may communicate via an intranet. Smaller organizations may handle password authentication internally but outsource fingerprint identification. Any combination of network-based local and/or remote communication is within the scope of the term "cloud" as used herein.

Figure 4:
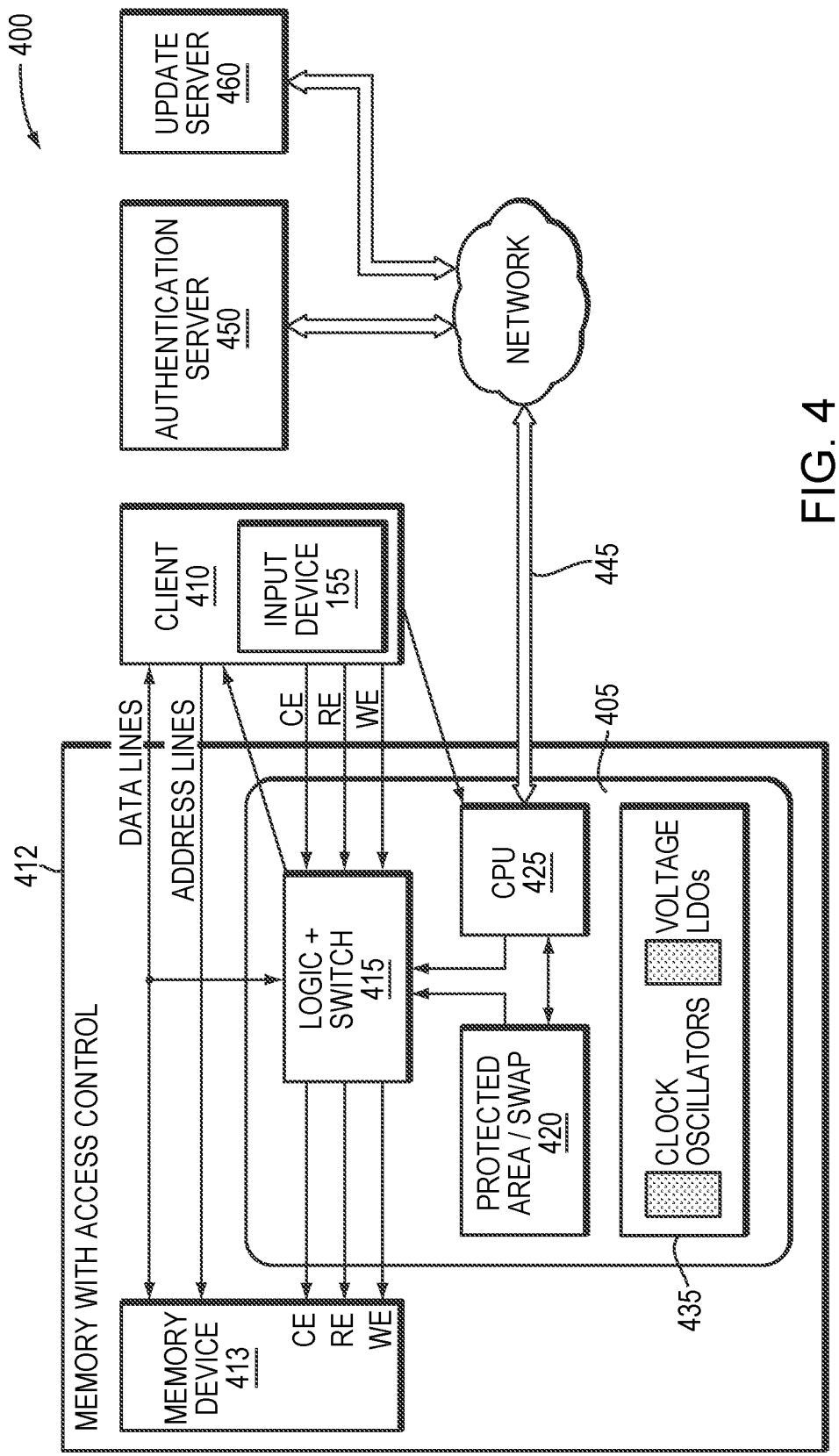
FIG. 4 schematically illustrates, in greater detail, an implementation of the security systems illustrated in FIGS. 3A and 3B.

Further details of a representative system 400 are shown in FIG. 4. In this implementation, the read/write control functionality is performed by an access-control circuit 405, which governs the ability of a client device 410 to interact with a storage facility 412, and in particular a memory device 413 thereon. For example, the storage facility may be FLASH device available to the client device 410 through standard bus and control lines. Of course, this is for illustrative purposes, and the storage facility 412 may in fact be part of the device 410, in either case the latter acts as a host and a client. More generally, the device 410 may be any device capable of interacting with memory device 413; thus, the device 410 may be a computer, a microprocessor, a controller, etc. The memory device 413 may be any type of volatile (e.g., random-access memory (RAM) or even cache memory) or non-volatile (e.g., Flash such as NOR Flash or NAND Flash) storage, and may be a single discrete device as illustrated or a series or "bank" of devices operating in tandem. Typically, the memory device 413 is chip-based and includes a matrix of memory cells addressed by a plurality of address lines and receiving or supplying data via a plurality of data lines (in some cases, the address and data lines share the same bus). It should be understood, however, that the present invention may also be used with control (e.g., microcontroller), processor (e.g., CPU), "system on chip" or other VLSI devices with resident or embedded memory—essentially any device that a device 410 may seek to access for purposes of data retrieval, data storage, and/or device operation.

In the illustrated system, the memory device 413 includes three control lines: chip enable (CE, sometimes referred to as "chip select"), read enable (RE) and write enable (WE). The client device 410 sends signals on these control lines to operate the memory 413. For example, suppose CE, RE and WE are enabled when high. To read data from the memory 413, the address of the byte to be fetched is presented on the address lines. CE and then RE are brought high, which enables the output on the data lines (which are normally tri-stated when CE is low). After a delay known as the access time, the contents of the byte in memory device 413 will be available on the data lines. After reading the data, CE and WE can be brought low again. To write a byte, its destination address is presented on the address lines. CE is brought high, the data to be written is applied to the address lines, and WE is brought high to write the data into memory.

In the illustrated system, the access-control circuit 405 intervenes between the CE, RE and WE control pins (or other interface hardware) on the memory device 413 and the complementary control pins on the client device 410. The lines connecting these control pins pass through a lock unit 415 that determines whether signals thereon will be allowed to pass between the memory device 413 and the client device 410. In addition, the lock unit 415 is passively connected to the data lines so as to be able to "listen," without disrupting or modifying, data signals thereon. Depending on the configuration, the lock unit 415 may include additional elements such as a secure internal data store 420 that may hold keys, access codes (e.g., shared secret, one-time pad ("OTP") codes, or other authentication codes), registers for data swapping or other operations, etc. A dedicated CPU 425 may be included to manage the internal data store 420 and implement the operations associated with the lock unit 415, and the circuitry may include other support elements generically indicated at 435 and including, for example, clock oscillators and voltage regulators. As noted above, the CPU 425 may also implement the proxy system as described above.

In FIG. 4, the memory device 413 and the lock unit 415 are shown within a single block, meaning that both elements 413, 415 reside within a single chip—e.g., the lock unit 415 may be implemented within and as part of the memory device 413, or both may be implemented as part of a processor chip or "system-on-chip" device. But other architectures are possible, e.g., the lock unit 415 may be a stand-alone chip (e.g., an ASIC) or may even be implemented within the client device 410. A representative lock unit is described in detail in the '316 application noted above.

The basic function of the lock unit 415 is to enforce a state-based security protocol that grants or changes the degree of access that the device 410 has to the memory device 413 only upon proper authentication. In fully local implementations, the device 410 provides a permission code to the lock unit 415 via the data lines; the lock unit 415 is always listening to signals on the data lines and reacts when it detects a data sequence (i.e., a bitstream) corresponding to a recognized command. These commands may instruct the lock unit 415 to report the current lock/unlock state (hereafter, for simplicity, a "lock state") on the data lines, change the lock state, or reprogram the functionality of the lock unit 415. In some embodiments, some or all commands are executed only if followed by a valid permission code, or in some implementations, if a command is received within an allowed interval following receipt of a valid permission code. The lock unit 415 may also implement measures to report or otherwise handle unauthorized permission codes. These measures may comprise an exclusion interval following detection of an unauthorized permission code during which the CPU 425 does not process codes subsequently presented on the data lines. The exclusion interval may increase with each unauthorized code detected (at least within a particular time interval) in order to thwart brute-force incursion attempts. Responsive measures may further include setting a flag or sending an alert, for example, upon detection of repeated unauthorized codes.

More broadly, authentication to the lock unit 415 may utilize schemes other than permission codes, and may not be fully internal. As shown in FIG. 4, the access-control circuit 405 (via the CPU 425 and a network interface 445) may communicate with a remote authentication server 450 via a computer network. As described above, the authentication server 450 implements an authentication policy, receiving credentials or other authentication data from the access-control circuit 405 (or, in some cases, client 410) via the network interface 445 and, more particularly, through a proxy or using another form of data security. The authentication server 450 determines whether the client 410 is entitled to access the protected memory 413. For example, the client 410 may have one or more input devices 455 that are used to obtain authentication credentials from a user. The input device may be one or more of a keyboard, which allows the user to enter a password; a fingerprint or vein reader, which allows the user to present a biometric indicium for analysis and matching; a token reader, such as a card or RFID reader, that interacts wirelessly with a physical token associated (e.g., in a user database maintained by the authentication server 450 or by a separate identity server) with the user; or other device.

For fingerprint-based biometric authentication, for example, the input device 455 is a scanner that reads a fingerprint and associated software (running on the client 410 or the access-control circuit 405) captures minutiae from the scanner. For password authentication, the client 410 may present an on-screen dialog box to capture either a static password or a one-time password from a token. Typically, the captured data is provided to the access-control circuit 405, which communicates it to the authentication server 450 for analysis and verification. The authentication server 450 may be, for example, a biometric identification server, a RADIUS server for token authentication, a KERBEROS server for "smartcard" log-on, or a physical access server for proximity-based card verification.

In operation, when the client 410 attempts to access memory device, the lock unit 415 signals the client 410 to obtain authentication information from the user. The information, obtained via keyboard input, a fingerprint scan or other authentication modality, is provided to the CPU 425 (e.g., via the data lines to the lock unit 415). The CPU 425 causes the received authentication information to be communicated to the authentication server 450, and upon confirmation from the server that authentication was successful, the CPU 425 causes the lock unit 415 to allow the memory request from the client 410 to be serviced and the memory 413 to be accessed. The authentication signal from the authentication server 450 may specify whether only read access or read/write access is to be accorded. The CPU 425 causes the state of the lock unit 415 to conform to the authentication signal, providing read access, read/write access, or no access if authentication fails.

The authentication server 450 may implement a security policy of any desired complexity, which may involve different modes (or multiple factors) of authentication for different users and depending on the nature of the data stored in the memory device 413. For example, sensitive data such as patient medical information may require "strong" authentication and the security policy may differentiate, for access purposes, among medical personnel. Thus, clinicians formally assigned to a patient's care team may be accorded full access to all patient data, while staff who administer a test may have access only to a portion of the patient's data and may lose access entirely after a period of time elapses unless further interaction with the patient has been detected. The authentication server 450 may be a single server or multiple servers each dedicated to a particular authentication factor.

As noted previously, the authentication server 450 may also handle tasks relating to encryption and secure communication. For example, the client 410 may store data in encrypted form in the memory device 413, and decryption may require the involvement of the authentication server. The authentication server 450 may, in some implementations, store the key complementary to that used to encrypt the data; if the user properly authenticates to the authentication server 450, the server decrypts the data retrieved from memory device 413 and provides it to the client 410.

In an "Internet of Things" (IoT) application, the authentication server 450 may be replaced by or interact (or simply coexist) with an update server 460, which manages updates to or replacement of the firmware for an IoT device. In this scenario, it may be the vendor's update server 460 rather than the client 410 that seeks access to memory 413 in order to install new firmware. The update server 460 may communicate with the access-control circuit 405 via the Internet (i.e., through the same channel employed by the user to interact with the device) or the public telecommunication infrastructure and authenticate using an access code recognized by the CPU 425 or the lock unit 415, subsequently sending new firmware to the IoT device or memory within the access-control circuit 405. The new firmware may be signed with a digital signature, which the lock unit 415 validates either directly or via communication with the authentication server 450. Once validated, the new firmware is stored in the memory device 413; if an entire new firmware image has been sent, it is executed to complete installation.

B. Applications

As noted, the present invention may be deployed across a wide range of embedded and stand-alone systems, particularly those that include an on-board memory store and interact with users via wired or wireless connections. The below focuses on representative applications.

B.1 Controllers

Figure 5:
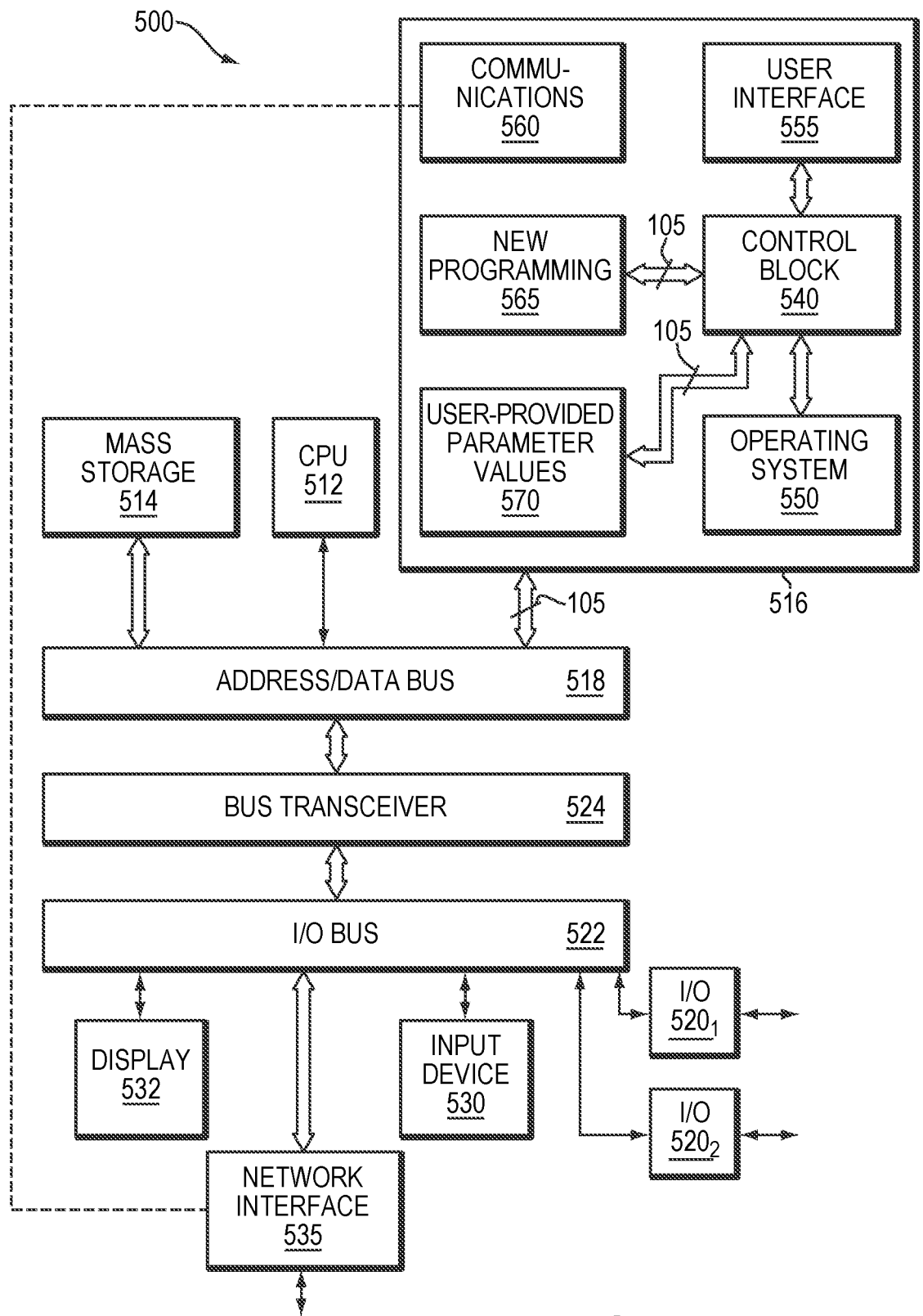
FIG. 5 schematically illustrates a programmable controller architecture in accordance with embodiments of the invention.

FIG. 5 illustrates a programmable controller architecture that may, depending on configuration and scaling, operate industrial machinery (e.g., valves in a refinery), a robot, an appliance, a medical device, a vehicle, or virtually any other device or system amenable to programmed control. The illustrated controller 500 includes a CPU (typically a microcomputer or microcontroller) 512 and one or more computer storage devices indicated generally at 514, 516. Ordinarily, the storage device 514 provides nonvolatile mass storage, and may be, for example, Flash and/or disk memory; and storage 516 comprises a combination of RAM for temporary storage and processing, and non-volatile, programmable read-only memory (PROM) that contains permanent aspects of the system's operating instructions.

The CPU 512 and computer storage 514, 516 communicate over an internal system bus 518. The controller 200 further includes a series of input/output (I/O) modules shown representatively at $520_1, 520_2$ that sense the condition of, and/or send control signals to, the controlled device over a machine interface. This machine interface, which may be as simple as a direct connection or can involve a communication link for interaction over a computer network or telephone lines, facilitates the bidirectional exchange of signals between each I/O module 520 and an associated device (e.g., a sensor or an actuator). Hence, the controller 500 may operate virtually any type of controlled device. The I/O modules 520 may, in some embodiments (particularly those involving industrial control), connect to a secondary I/O bus 522, which is driven by a bus transceiver 524; in effect, the buses 518, 522 and bus transceiver 524 form a single logical bus.

Optionally, the controller 500 may include one or more input devices 530, also connected to the I/O bus 522, that permit the operator to program the controller and/or enter information. The output of either device can be used to designate information or to select particular areas of a screen display 532. In some implementations, the input devices 530 may include a keyboard and a position-sensing device such as a mouse. In embedded implementations, by contrast, the controller 500 typically includes no display or peripheral devices, and a user's interaction with the controller 500 occurs via a wired or wireless connection—e.g., using a general-purpose device such as a "smart phone" or tablet running a program (or "app") configured to establish communication with the controller 500 and provide the user interface on its own display. A conventional network interface 535, which may be wired (e.g., ETHERNET) or wireless (e.g., 802.11x or cellular) or, in some embodiments, provide for both wired and wireless communications, also transmits and receives signals via I/O bus 522.

Storage 516 contains a series of functional blocks or modules that implement the functions performed by controller 500 through operation of the CPU 512. A control block 540 contains computer-executable instructions for actually operating controlled equipment via the I/O modules 520, as well as storing data gathered by the controller 500 via the I/O modules. The control block 540 contains both the specific high-level instructions for operating the controller 500, including selecting among control functions if multiple functions are supported, and the compiler (or interpreter) module for translating these into instructions processed by the CPU 512. Storage 516 includes an operating system 550, which directs the execution of low-level, basic system functions such as memory allocation, file management and operation of storage device 514; and instructions defining a user interface 555, which may, again, drive a local display 532 or merely supply data to an interface program running on a separate device, but in any case providing status information and accepting operator commands. A communications module 560 drives the network interface 535 via the I/O bus 522 to receive signals from outside devices and transmit signals to outside devices.

Supporting the user's ability to interact with and configure the controller 500 are a pair of memory partitions 565, 570. The memory partition 565 stores user programming, e.g., portions or even the entirety of the control block 540 that defines the functionality of the controller 500 and operates the CPU 512. General-purpose microcontrollers, for example, allow the user to completely specify the operation of the device, even the functionality of individual I/O ports, by writing the control program that the device executes; in these implementations, the partition 565 may contain the entire control program. Embedded microcontrollers contain application-specific software and, often, hardware, but may allow the user to select, replace or modify particular portions of the program. In such implementations, the partition 565 may contain libraries or program modules that the user can modify or replace. The memory partition 570 stores configuration parameter values selected by the user (e.g., schedule settings for a thermostat, administration profiles for an implanted medicinal pump, etc.).

An access-control circuit 405 as illustrated in FIG. 4 may be deployed at one or more locations within the architecture of the controller 500. In some embodiments, particularly when storage 516 (or, e.g., the volatile portion thereof) is deployed on a single chip, the access-control circuit 405 is disposed between the address/data bus 518 and the entire storage 516. This results in a gatekeeping function across all memory interactions, which may not be desired. Instead, the access-control circuit 405 may be situated so as to govern access only to one or both of the memory partitions 565, 570. These partitions may be deployed on separate chips, on a single separate chip, or as logical partitions of a single memory unit. The access-control unit 405 is readily adapted to any of these configurations, and can govern interaction with a portion of a memory chip or chipset by, for example, establishing the portion of the memory to be used, listening on the address lines, and activating/deactivating the access-control unit 405 according to the lock/unlock state for the relevant portion of memory.

Operation of the access-control unit 405 is as described above. Alternatively or in addition, the lock/unlock state may be set manually by a properly authenticated user via the user interface 555 and programming in the control block 540 and/or controller-access programming running on a wireless user device. Similarly, this programming may allow the user, via the user interface 555, to reprogram the state transitions, permission codes and other governing attributes of the access-control unit 405. In some embodiments, the user may interact with the controller 500 using an external device, such as a tablet, via the network interface 535. In these implementations, the external device acts as the management server described above. In addition to reprogramming the controller via the external device, the user may view telemetry data obtained by the controller 500 via sensors connected to one or more of the I/O ports 520. This permits the user both to view the current state of the controlled system as well as monitor the effects of reprogramming as it takes effect. As discussed above, the telemetry data may be cached in storage 516.

In order to ensure secure communications between an external device and the controller 500, the access-control unit 405 or the CPU 512 may implement proxy functionality as discussed above. Data transmitted via the trusted channel implemented by the proxy system is unavailable to applications executed by the CPU 512. The proxy system may require authentication via the external user device, either directly (via a fingerprint reader, for example) or indirectly via an authentication server using credentials supplied by the user via the external device.

B.2 Smart Appliances and "Internet of Things" Applications

The so-called "Internet of Things" (IoT) refers broadly to the interconnection via the Internet of computing devices embedded in everyday appliances and devices, enabling them to send and receive data. Users can control IoT-enabled household systems such as heating and ventilation systems, sprinkler systems and home-security systems using a smart phone or other Internet-connected device. More broadly, farmers use IoT systems to monitor water quality and atmospheric and soil conditions, and transportation authorities monitor real-time traffic patterns to alter traffic-signal timing. Such capabilities greatly expand convenience and flexibility, but like any functionality accessible over the Internet, pose security and privacy risks. The consequences of a successful hack of a residential or commercial alarm system are obvious, but even for applications that do not involve critical systems, the potential for harm is significant. IoT devices may store passwords, credit-card numbers or other sensitive data to facilitate convenient upgrades, and researchers have demonstrated the ability to intercept unencrypted data from a smart meter device to determine what television show someone was watching at that moment.

Figure 6:
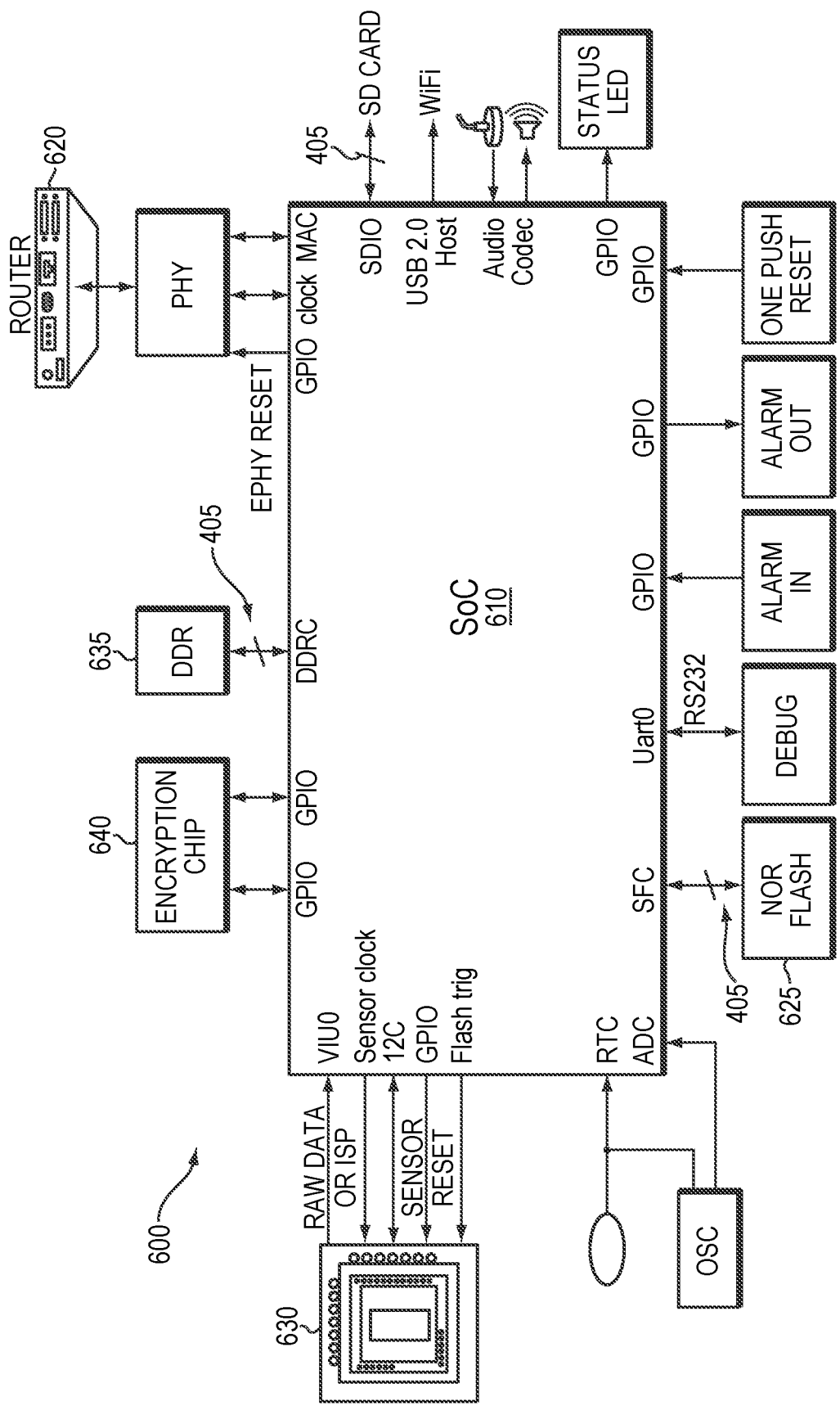
FIG. 6 schematically illustrates a representative "Internet of Things" deployment of an embodiment of the invention.

One widely used IoT application is an IP (Internet Protocol) camera used primarily for surveillance. Unlike analog closed-circuit television (CCTV) cameras, an IP camera can send and receive data via a computer network such as the Internet. FIG. 6 illustrates an IP camera system 600 that utilizes a SoC 610 (such as the Hi3518C SoC supplied by HiSilicon Technologies, Ltd.) and a conventional image sensor 615. The SoC 610 receives image data from the image sensor 615 and creates high-definition video for transmission over IP via a router 620, e.g., to the management server 310 shown in FIGS. 3A and 3B. IP camera SoC devices include processing capacity to execute image processing and encoding, and may support additional features such as lens distortion correction. Firmware implementing these functions is stored in a non-volatile NOR Flash memory 625, with which the SoC 610 interacts via an SPI Flash controller (SFC). The Flash memory 625 may be accessed by the management server 310 via the router 620 and the physical (PHY) layer, for example, to permit the SoC vendor to replace or modify the firmware stored thereon. User identity or password information may also be stored in the NOR Flash memory 625. Although a commercial IP camera SoC typically does not accommodate user modification to the internal programming, other IoT devices may allow the user to select, replace or modify particular portions of the firmware.

The SoC 610 may also include interfaces for external memory and removable memory cards. For example, an SDIO interface connects an internal memory controller to a non-volatile memory card, e.g., a Secure Digital (SD) memory card 630. When the SD card 630 is detected, the SDIO interface becomes active, storing on the SD card successive frames of image data received from the image sensor 615 for later playback. A DDRC interface connects an internal memory controller of SoC 610 to a permanent bank of volatile memory 635 (e.g., double data rate synchronous dynamic RAM) to accommodate integration of the SoC 610 in devices, such as computers or stand-alone cameras, that include on-board volatile memory. Once again, when external memory is connected to the SoC 610 via the DDRC interface, frames of image data received from the image sensor 615 are stored in the external memory.

The access-control circuit 405 may be deployed across the data and/or control lines of one or more of the DDRC, SDIO or SFC. For example, if the SoC 610 is configured to read and write memory over a single memory bus (see FIG. 5), the access-control circuit 405 may be connected to "listen" to the data lines of the memory bus and to switch the control lines of the SDIO, DDR and/or Flash memory controllers. Connection across the Flash memory control and/or data lines prevents an attacker from gaining access to the SoC firmware and, if present, stored user data by "spoofing"—that is, posing as the vendor or other authorized party and reading or writing the data in the Flash memory 625 via the router 620. Connection across the data and/or control lines between the SD card or external memory and the SoC 610 prevents an attacker from accessing stored video data (e.g., once again, by communicating with the SoC 610 via the router 620 and posing as an authorized user). For example, a thief may utilize access to a video feed from a surveillance camera to determine when the monitored premises are empty of occupants and therefore vulnerable.

More generally, for IoT devices, the access-control circuit 405 can be integrated within a SoC or deployed as a separate component on the device printed circuit board to protect memory that can be accessed by routine user command or by the vendor with an enhanced permission level (which can be spoofed).

A user may interact with the camera system 600 using an external device, such as a smart phone or tablet executing an application ("app"), via the PHY layer. In these implementations, the external device acts as the management server described above. In this way, the user may reprogram the camera system 600, e.g., to change its orientation, image-acquisition rate, etc. The user may also view real-time or cached images acquired by the camera 600. This permits the user both to see what the camera sees and to observe the effects of altering camera settings as they take effect.

In order to ensure secure communications between an external device and the camera system 600, the SoC 610 may implement proxy functionality as discussed above, utilizing, for example, an encryption chip 640. Data transmitted via the trusted channel implemented by the proxy system is unavailable to applications accessing the camera system 600 via the router 620. The proxy system may require authentication via the external user device, either directly (via a fingerprint reader, for example) or indirectly via an authentication server using credentials supplied by the user via the external device.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A security system for servicing memory access requests from a client device including a network interface, the security system comprising:
   a. a protected device comprising a central processing unit, memory and a lock unit connected to the memory, the lock unit comprising a network interface; and
   b. an authentication server,
   wherein the lock unit is configured to (i) detect a memory access request from the client device, (ii) receive authentication data from the client device and communicate the received authentication data to the authentication server via the network interface, and (iii) only upon receipt via the network interface of an authentication confirmation signal from the authentication server, cause the lock unit to allow the memory access request to be serviced, and further wherein the network interface is isolated from the central processing unit of the protected device.

2. The system of claim 1, wherein the authentication data is a password/certificate symmetric or asymmetric.

3. The system of claim 1, wherein the authentication data is a biometric indicium.

4. The system of claim 1, wherein the authentication signal specifies read access, read/write access or no access, the processor being configured to responsively operate the lock unit in accordance with the authentication confirmation signal.

5. The system of claim 1, wherein the authentication server is remote from the protected device.

6. A protected digital device comprising:
   a. a processor;
   b. a memory;
   c. a communication platform;
   d. a security system for servicing access requests to the memory;
   e. a lock unit connected to the memory; and
   f. a proxy system for establishing a trusted communication channel via the communication platform between the lock unit and an authentication server external to the protected digital device,
   wherein the lock unit is configured to (i) detect a memory access request from the processor, (ii) communicate authentication data to the authentication server via the trusted communication channel, and (iii) only upon receipt via the trusted communication channel of an authentication confirmation signal from the authentication server, cause the lock unit to allow the memory access request to be serviced, and further wherein the trusted communication channel is isolated from the processor.

7. The system of claim 6, wherein the authentication data is a password or certificate encrypted symmetrically or asymmetrically.

8. The system of claim 6, wherein the authentication data is a biometric indicium.

9. The system of claim 6, wherein the authentication signal specifies read access, read/write access or no access, the processor being configured to responsively operate the lock unit in accordance with the authentication confirmation signal.

10. The system of claim 6, wherein the proxy system provides end-to-end encryption between the authentication server and the lock unit.

11. The system of claim 6, wherein the proxy system provides symmetric encryption between the authentication server and the lock unit.

12. The system of claim 6, wherein the proxy system is configured to examine communications received from the authentication server for a digital signature.

13. A security system for servicing memory access requests from a client device having a central processing unit, the security system comprising:
   a. on the client device, (i) a protected device comprising memory and a lock unit connected thereto, (ii) a proxy system, and (iii) a communication platform; and
   b. a management server for performing a management function comprising receiving and processing signals from the client device, the communication platform including a proxy system for establishing a trusted communication channel between the management server and the lock unit, wherein the lock unit is configured to (i) detect a valid memory access request provided via the trusted communication channel, and (ii) allow the memory access request to be serviced and data transmitted to the management server over the trusted communication channel, and further wherein the trusted communication channel is isolated from the central processing unit of the host device.

14. The system of claim 13, wherein the trusted communication channel is established via symmetric encryption.

15. The system of claim 13, wherein the trusted communication channel is established via end-to-end encryption.

16. The system of claim 13, wherein the management server is configured to provide an authentication function that includes receiving authentication data from the client device and allowing establishment of the trusted communication channel only following validation of the received authentication data.

17. The system of claim 13, wherein the memory access request includes data specifying read access, read/write access or no access, the lock unit responsively operating in accordance with the data included in the memory access request.

18. The system of claim 13, wherein the lock unit is responsive only to write commands issued by the management server.

19. The system of claim 13, wherein the client device comprises a processor, the lock unit being responsive only to write commands issued by the client processor only following receipt via the trusted channel of a valid memory access request including a write permission for the processor.

20. The system of claim 13, wherein the client device is configured to generate telemetry data, cache the telemetry data in the protected device memory, and transmit the telemetry data to the management server via the trusted communication channel.

21. The system of claim 13, wherein the client device comprises a processor, the processor not having access to the telemetry data.

* * * * *